(12) United States Patent
Loschak et al.

(10) Patent No.: US 12,358,144 B2
(45) Date of Patent: Jul. 15, 2025

(54) SYSTEM AND METHOD FOR ERROR HANDLING IN A SURGICAL ROBOTIC SYSTEM

(71) Applicant: Covidien LP, Mansfield, MA (US)

(72) Inventors: Paul Loschak, Somerville, MA (US); Walter Schoen, Cambridge, MA (US); Srilalitha Kumaresan, Brookline, MA (US); Andreas Tobergte, Munich (DE); Stefan Joerg, Munich (DE)

(73) Assignee: Covidien LP, Mansfield, MA (US)

( * ) Notice: Subject to any disclaimer, the term of this patent is extended or adjusted under 35 U.S.C. 154(b) by 294 days.

(21) Appl. No.: 17/913,199

(22) PCT Filed: Mar. 9, 2021

(86) PCT No.: PCT/US2021/021432
§ 371 (c)(1),
(2) Date: Sep. 21, 2022

(87) PCT Pub. No.: WO2021/211225
PCT Pub. Date: Oct. 21, 2021

(65) Prior Publication Data
US 2023/0166405 A1    Jun. 1, 2023

Related U.S. Application Data

(60) Provisional application No. 63/010,270, filed on Apr. 15, 2020.

(51) Int. Cl.
*B25J 9/16* (2006.01)
*A61B 34/00* (2016.01)
(Continued)

(52) U.S. Cl.
CPC ............. *B25J 9/1689* (2013.01); *A61B 34/25* (2016.02); *A61B 34/37* (2016.02); *A61B 50/13* (2016.02); *B25J 9/1674* (2013.01)

(58) Field of Classification Search
CPC ....... B25J 9/1689; B25J 9/1674; A61B 34/25; A61B 34/37; A61B 50/13;
(Continued)

(56) References Cited

U.S. PATENT DOCUMENTS

| 5,231,693 A * | 7/1993 | Backes | B25J 9/1661 318/568.1 |
| 8,004,229 B2 * | 8/2011 | Nowlin | B25J 9/1689 318/568.2 |

(Continued)

FOREIGN PATENT DOCUMENTS

| WO | 2006124390 A2 | 11/2006 |
| WO | 2014022786 A2 | 2/2014 |

(Continued)

OTHER PUBLICATIONS

International Search Report and Written Opinion dated Jun. 16, 2021 issued in corresponding PCT Appln. No. PCT/US2021/021432.

*Primary Examiner* — Rachid Bendidi
*Assistant Examiner* — Nada Mahyoob Alqaderi
(74) *Attorney, Agent, or Firm* — Carter, DeLuca & Farrell LLP

(57) ABSTRACT

A surgical robotic system includes: a control tower including a first controller configured to detect a first error associated with the control tower and having a first error handler configured to generate a first error signal based on the first error. The system includes a console coupled to the control tower and including a display, a user input device configured to generate user input, and a mobile cart coupled to the control tower and having a second controller configured to detect a second error associated with the mobile cart and a second error handler configured to generate a second error signal based on the second error. The system includes a robotic arm disposed on the mobile cart and including: a (Continued)

surgical instrument configured to treat tissue and actuatable in response to the user input; and a third controller configured to detect a third error associated with the surgical robotic arm and having a third error handler configured to generate a third error signal based on the third error.

16 Claims, 6 Drawing Sheets

(51) Int. Cl.
*A61B 34/37* (2016.01)
*A61B 50/13* (2016.01)

(58) Field of Classification Search
CPC .... A61B 2560/0271; A61B 2560/0276; A61B 34/30; G05B 2219/45117
See application file for complete search history.

(56) References Cited

U.S. PATENT DOCUMENTS

| | | |
|---|---|---|
| 2006/0241414 A1 | 10/2006 | Nowlin et al. |
| 2017/0000577 A1* | 1/2017 | Bowling .................. B25J 13/00 |
| 2019/0143513 A1* | 5/2019 | Rabindran ............. B25J 9/1607 |
| | | 700/245 |

FOREIGN PATENT DOCUMENTS

| | | | |
|---|---|---|---|
| WO | 2015142796 A1 | 9/2015 | |
| WO | WO-2019152761 A1 * | 8/2019 | ............. A61B 34/37 |

* cited by examiner

SYSTEM AND METHOD FOR ERROR HANDLING IN A SURGICAL ROBOTIC SYSTEM

CROSS REFERENCE TO RELATED APPLICATIONS

The present application is a National Stage Application under 35 U.S.C. § 371(a) of PCT/US2021/021432, filed Mar. 9, 2021, which claims the benefit of and priority to U.S. Patent Provisional Application No. filed 63/010,270 filed on Apr. 15, 2020. The entire disclosures of the foregoing applications are incorporated by reference herein.

BACKGROUND

Surgical robotic systems are currently being used in minimally invasive medical procedures. Some surgical robotic systems include a surgical console controlling a surgical robotic arm and a surgical instrument having an end effector (e.g., forceps or grasping instrument) coupled to and actuated by the robotic arm.

Each of the components, e.g., surgical console, robotic arm, etc., of the surgical robotic system may be controlled by a computing device, which communicate with each other through a communication network. Thus, when one of the computing devices or a component of the surgical robotic system experiences an error, such error needs to be propagated through the entire surgical robotic system and all of its components, since an error may be localized or affect other components and/or the entire surgical robotic system. Accordingly, there is a need for an error handler subsystem for use with surgical robotic systems.

SUMMARY

The present disclosure provides a surgical robotic system including a plurality of components, namely, a control tower, a console, and one or more surgical robotic arms, each of which is disposed on a movable cart and includes a surgical instrument. Each of the robotic arms is operable in one or more control modes, e.g., hold mode, movement mode, position control mode etc. The surgical robotic system includes an error handler subsystem, which is configured to transmit error signals between each of the components, such that each of the components is notified of the error signal generated by another component. In embodiments, error signals are transmitted between the core tower, surgical console, and arm cart assemblies to determine which control mode should be disallowed. Certain error signals may result in either short term (e.g., from about 1 second to about 5 seconds) interruptions or long-term blockers. Short term interruptions are configured to interrupt position control of the robotic arm or other control of the component and long-term blockers are configured to permanently end position control until the system is rebooted or malfunctioning components are replaced. In further embodiments, certain error signals may result in disabling manual bedside control of the robotic arms, surgical console ergonomic controls, and/or other aspects of manually commanded motion.

The error handler subsystem also sends specific notification codes to an alarms and notifications subsystem, which is configured to display messages and other indicators to the users of the surgical robotic system. Each of the error signals may include one or more error states indicating prohibited actions as well a counter that is matched between the components to confirm receipt of the error signal, which acts as a handshake between the components. The error handler subsystem coordinates short term interruptions and long-term blockers as well as safe reactions to the error signals occurring at any components of the system.

According to one embodiment of the present disclosure, a surgical robotic system is disclosed. The surgical robotic system includes: a control tower including a first controller having a first error handler. The first controller is configured to detect a first error associated with the control tower and the first error handler is configured to generate a first error signal based on the first error. The system also includes a surgical console coupled to the control tower. The surgical console includes a display and a user input device configured to generate a user input. The system further includes a mobile cart coupled to the control tower. The mobile cart includes a second controller and a second error handler. The second controller is configured to detect a second error associated with the mobile cart and the second error handler is configured to generate a second error signal based on the second error. The system also includes a surgical robotic arm disposed on the mobile cart. The surgical robotic arm includes: a surgical instrument configured to treat tissue and being actuatable in response to the user input; and a third controller having a third error handler. The third controller is configured to detect a third error associated with the surgical robotic arm and the third error handler is configured to generate a third error signal based on the third error.

According to one aspect of the above embodiment, the surgical robotic arm is operable in a position control mode in response to the user input and a manual mode in response to manual movement.

According to another aspect of the above embodiment, the system further includes an error handler network interconnecting the first error handler, the second error handler, and the third error handler, the error handler network configured to transmit the first error signal, the second error signal, and the third error signal between the first error handler, the second error handler, and the third error handler. The error handler network is configured to categorize one of the first error signal, the second error signal, and the third error signal and to perform a response based on categorization. The response may include temporarily interrupting the manual mode and disabling the position control mode.

According to a further aspect of the above embodiment, one or more the following, namely, the control tower, the surgical console, or the mobile cart may include a display. The system may further include an alarm and notification subsystem coupled to the error handler network, the alarm and notification subsystem configured to display a notification on the display. The error handler network is configured to reenable at least one the manual mode and the position control mode after the notification is dismissed by a user. The error handler network is configured to store a counter that is incremented in response to at least one of temporary interruption of the manual mode and disabling of the position control mode. Each of the first error handler, the second error handler, and the third error handler stores an individual counter that is incremented in response to incrementing any of the individual counters.

According to another embodiment of the present disclosure, a surgical robotic system is disclosed. The surgical robotic system includes a control tower including a first controller having a first error handler. The first controller is configured to detect a first error associated with the control tower and the first error handler is configured to generate a first error signal based on the first error. The system also includes a surgical console coupled to the control tower. The surgical console includes a display and a user input device configured to generate a user input. The system also includes a plurality of mobile carts coupled to the control tower, each of the mobile carts including a second controller and a second error handler. The second controllers are configured to detect a second error associated with the mobile cart and the second error handlers are configured to generate a second error signal based on the second error. The system also includes a plurality of surgical robotic arms, each of the surgical robotic arms is disposed on one mobile cart of the plurality of mobile carts. Each of the surgical robotic arm includes a surgical instrument configured to treat tissue and being actuatable in response to the user input and a third controller having a third error handler. The third controller is configured to detect a third error associated with the surgical robotic arm and the third error handler are configured to generate a third error signal based on the third error.

According to one aspect of the above embodiment, the surgical robotic arms are operable in a position control mode in response to the user input and a manual mode in response to manual movement.

According to another aspect of the above embodiment, the system further includes an error handler network interconnecting the first error handler, the second error handler, and the third error handler, the error handler network configured to transmit the first error signal, the second error signal, and the third error signal between the first error handler, the second error handler, and the third error handler. The error handler network is configured to categorize one of the first error signal, the second error signal, and the third error signal and to perform a response based on categorization. The response includes temporarily interrupting the manual mode and disabling the position control mode.

According to a further aspect of the above embodiment, one or more of the following, namely, the control tower, the surgical console, one of the mobile carts, includes a display. The system further includes an alarm and notification subsystem coupled to the error handler network, the alarm and notification subsystem configured to display a notification on the display. The error handler network is configured reenable at least one the manual mode and the position control mode after the notification is dismissed by a user. The error handler network is configured to store a counter that is incremented in response to at least one of temporary interruption of the manual mode and disabling of the position control mode. Each of the first error handler, the second error handler, and the third error handler stores an individual counter that is incremented in response to incrementing any of the individual counters.

According to another aspect of the above embodiment, the surgical console includes a fourth controller having a fourth error handler, the fourth controller configured to detect a fourth error associated with the surgical console and the fourth error handler is configured to generate a fourth error signal based on the fourth error.

BRIEF DESCRIPTION OF THE DRAWINGS

Embodiments of the present disclosure are described herein with reference to the accompanying drawings, wherein.

DETAILED DESCRIPTION

Figure 1:
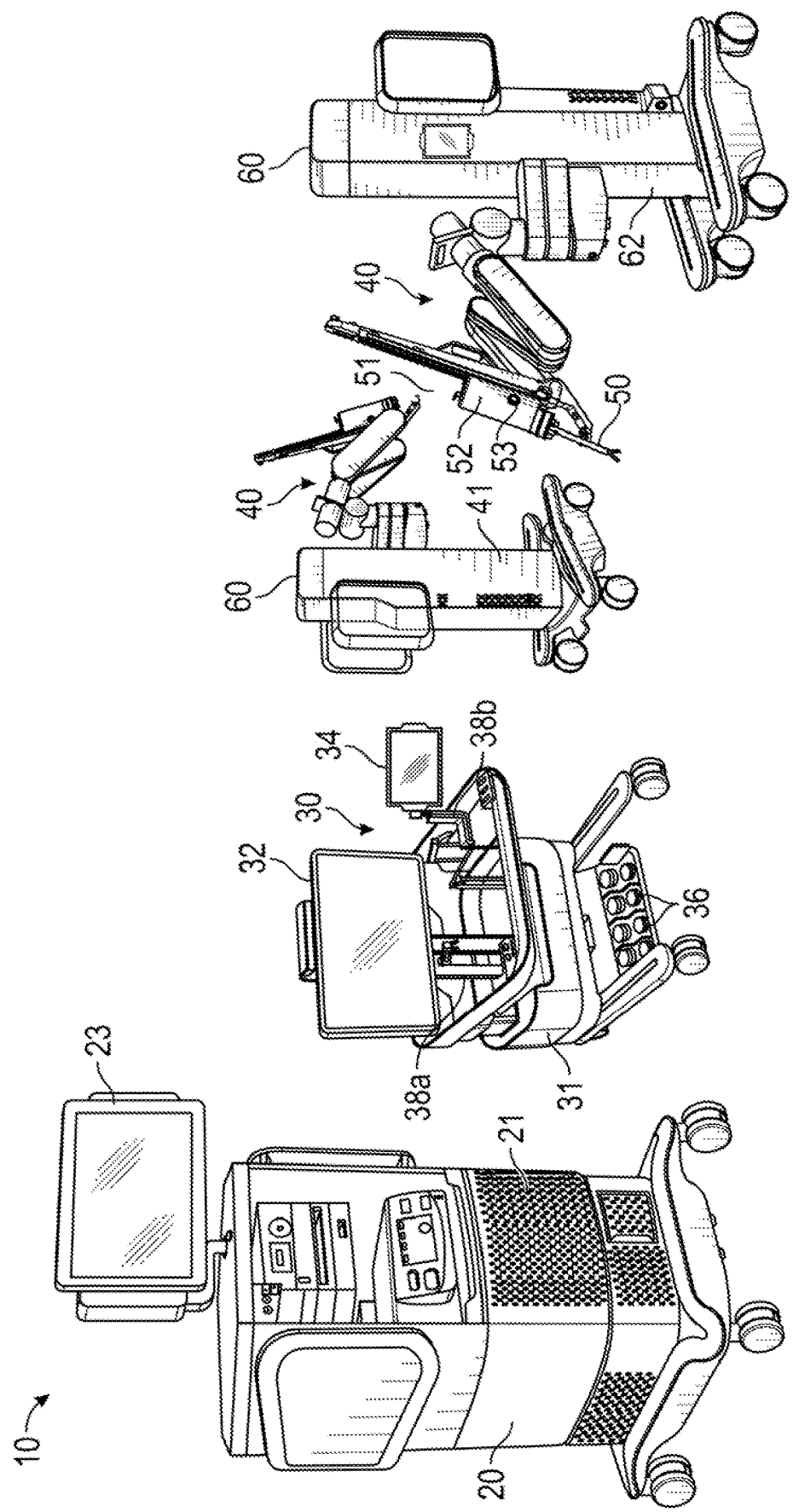
FIG. 1 is a schematic illustration of a surgical robotic system including a control tower, a console, and one or more surgical robotic arms according to the present disclosure.

Embodiments of the presently disclosed surgical robotic system are described in detail with reference to the drawings, in which like reference numerals designate identical or corresponding elements in each of the several views. As used herein the term "distal" refers to the portion of the surgical robotic system and/or the surgical instrument coupled thereto that is closer to the patient, while the term "proximal" refers to the portion that is farther from the patient.

The term "application" may include a computer program designed to perform functions, tasks, or activities for the benefit of a user. Application may refer to, for example, software running locally or remotely, as a standalone program or in a web browser, or other software which would be understood by one skilled in the art to be an application. An application may run on a controller, or on a user device, including, for example, a mobile device, an IOT device, or a server system.

As will be described in detail below, the present disclosure is directed to a surgical robotic system, which includes a surgical console, a control tower, and one or more movable carts having a surgical robotic arm coupled to a setup arm. The surgical console receives user input through one or more interface devices, which are interpreted by the control tower as movement commands for moving the surgical robotic arm. The surgical robotic arm includes a controller, which is configured to process the movement command and to generate a torque command for activating one or more actuators of the robotic arm, which would, in turn, move the robotic arm in response to the movement command.

With reference to FIG. 1, a surgical robotic system 10 includes a control tower 20, which is connected to all of the components of the surgical robotic system 10 including a surgical console 30 and one or more robotic arms 40. Each of the robotic arms 40 includes a surgical instrument 50 removably coupled thereto. Each of the robotic arms 40 is also coupled to a movable cart 60.

The surgical instrument 50 is configured for use during minimally invasive surgical procedures. In embodiments, the surgical instrument 50 may be configured for open surgical procedures. In embodiments, the surgical instrument 50 may be an endoscope configured to provide a video feed for the user. In further embodiments, the surgical instrument 50 may be an electrosurgical forceps configured to seal tissue by compression tissue between jaw members and applying electrosurgical current thereto. In yet further embodiments, the surgical instrument 50 may be a surgical stapler including a pair of jaws configured to grasp and clamp tissue whilst deploying a plurality of tissue fasteners, e.g., staples, and cutting stapled tissue.

Each of the robotic arms 40 may include a camera 51 configured to capture video of the surgical site. The camera 51 may be a stereoscopic camera and may be disposed along with the surgical instrument 50 on the robotic arm 40. The surgical console 30 includes a first display 32, which displays a video feed of the surgical site provided by camera 51 of the surgical instrument 50 disposed on the robotic arms 40, and a second display device 34, which displays a user interface for controlling the surgical robotic system 10. The surgical console 30 also includes a plurality of user interface devices, such as foot pedals 36 and a pair of handle controllers 38a and 38b which are used by a user to remotely control robotic arms 40.

The control tower 20 includes a display 23, which may be a touchscreen, and outputs on the graphical user interfaces (GUIs). The control tower 20 also acts as an interface between the surgical console 30 and one or more robotic arms 40. In particular, the control tower 20 is configured to control the robotic arms 40, such as to move the robotic arms 40 and the corresponding surgical instrument 50, based on a set of programmable instructions and/or input commands from the surgical console 30, in such a way that robotic arms 40 and the surgical instrument 50 execute a desired movement sequence in response to input from the foot pedals 36 and the handle controllers 38a and 38b.

Each of the control tower 20, the surgical console 30, and the robotic arm 40 includes a respective computer 21, 31, 41. The computers 21, 31, 41 are interconnected to each other using any suitable communication network based on wired or wireless communication protocols. The term "network," whether plural or singular, as used herein, denotes a data network, including, but not limited to, the Internet, Intranet, a wide area network, or a local area networks, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 802.15.4-2003 standard for wireless personal area networks (WPANs)).

The computers 21, 31, 41 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Figure 2:
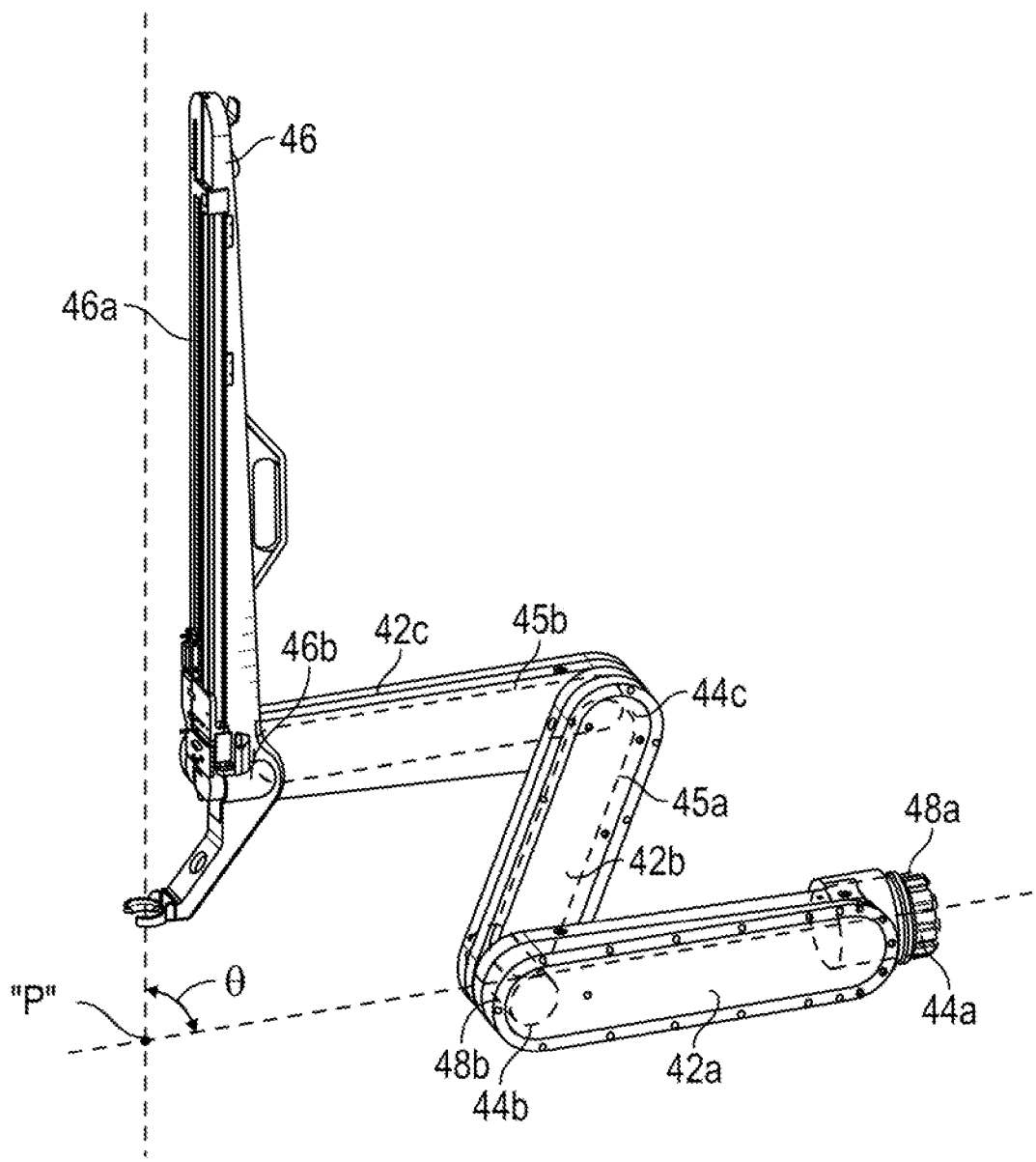
FIG. 2 is a perspective view of a surgical robotic arm of the surgical robotic system of FIG. 1 according to the present disclosure.
Figure 3:
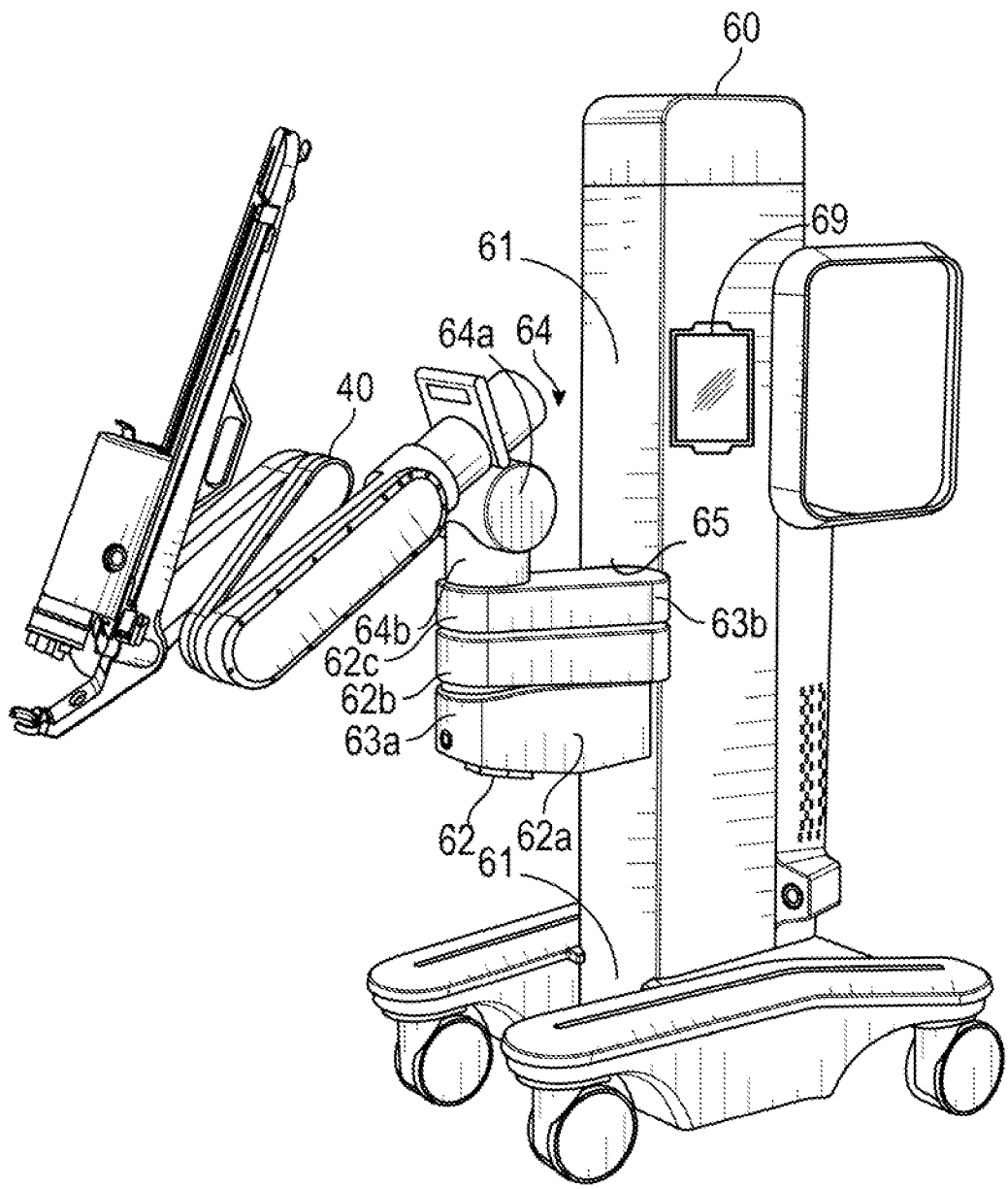
FIG. 3 is a perspective view of a setup arm with the surgical robotic arm of the surgical robotic system of FIG. 1 according to the present disclosure.

With reference to FIG. 2, each of the robotic arms 40 may include a plurality of links 42a, 42b, 42c, which are interconnected at joints 44a, 44b, 44c, respectively. The joint 44a is configured to secure the robotic arm 40 to the movable cart 60 and defines a first longitudinal axis. With reference to FIG. 3, the movable cart 60 includes a lift 61 and a setup arm 62, which provides a base for mounting of the robotic arm 40. The lift 61 allows for vertical movement of the setup arm 62. The movable cart 60 also includes a display 69 for displaying information pertaining to the robotic arm 40.

The setup arm 62 includes a first link 62a, a second link 62b, and a third link 62c, which provide for lateral maneuverability of the robotic arm 40. The links 62a, 62b, 62c are interconnected at joints 63a and 63b, each of which may include an actuator (not shown) for rotating the links 62b and 62b relative to each other and the link 62c. In particular, the links 62a, 62b, 62c are movable in their corresponding lateral planes that are parallel to each other, thereby allowing for extension of the robotic arm 40 relative to the patient (e.g., surgical table). In embodiments, the robotic arm 40 may be coupled to the surgical table (not shown). The setup arm 62 includes controls 65 for adjusting movement of the links 62a, 62b, 62c as well as the lift 61.

The third link 62c includes a rotatable base 64 having two degrees of freedom. In particular, the rotatable base 64 includes a first actuator 64a and a second actuator 64b. The first actuator 64a is rotatable about a first stationary arm axis which is perpendicular to a plane defined by the third link 62c and the second actuator 64b is rotatable about a second stationary arm axis which is transverse to the first stationary arm axis. The first and second actuators 64a and 64b allow for full three-dimensional orientation of the robotic arm 40.

The robotic arm 40 also includes a plurality of manual override buttons 53 disposed on instrument drive unit 52 and the setup arm 62, which may be used in a manual mode. The user may press one or the buttons 53 to move the component associated with the button 53.

With reference to FIG. 2, the robotic arm 40 also includes a holder 46 defining a second longitudinal axis and configured to receive the instrument drive unit 52 (FIG. 1) of the surgical instrument 50, which is configured to couple to an actuation mechanism of the surgical instrument 50. Instrument drive unit 52 transfers actuation forces from its actuators to the surgical instrument 50 to actuate components (e.g., end effectors) of the surgical instrument 50. The holder 46 includes a sliding mechanism 46a, which is configured to move the instrument drive unit 52 along the second longitudinal axis defined by the holder 46. The holder 46 also includes a joint 46b, which rotates the holder 46 relative to the link 42c.

The joints 44a and 44b include an actuator 48a and 48b configured to drive the joints 44a, 44b, 44c relative to each other through a series of belts 45a and 45b or other mechanical linkages such as a drive rod, a cable, or a lever and the like. In particular, the actuator 48a is configured to rotate the robotic arm 40 about a longitudinal axis defined by the link 42a.

The actuator 48b of the joint 44b is coupled to the joint 44c via the belt 45a, and the joint 44c is in turn coupled to the joint 46c via the belt 45b. Joint 44c may include a transfer case coupling the belts 45a and 45b, such that the actuator 48b is configured to rotate each of the links 42b, 42c and the holder 46 relative to each other. More specifically, links 42b, 42c, and the holder 46 are passively coupled to the actuator 48b which enforces rotation about a pivot point "P" which lies at an intersection of the first axis defined by the link 42a and the second axis defined by the holder 46. Thus, the actuator 48b controls the angle θ between the first and second axes allowing for orientation of the surgical instrument 50. Due to the interlinking of the links 42a, 42b, 42c, and the holder 46 via the belts 45a and 45b, the angles between the links 42a, 42b, 42c, and the holder 46 are also adjusted in order to achieve the desired angle θ. In embodiments, some or all of the joints 44a, 44b, 44c may include an actuator to obviate the need for mechanical linkages.

Figure 4:
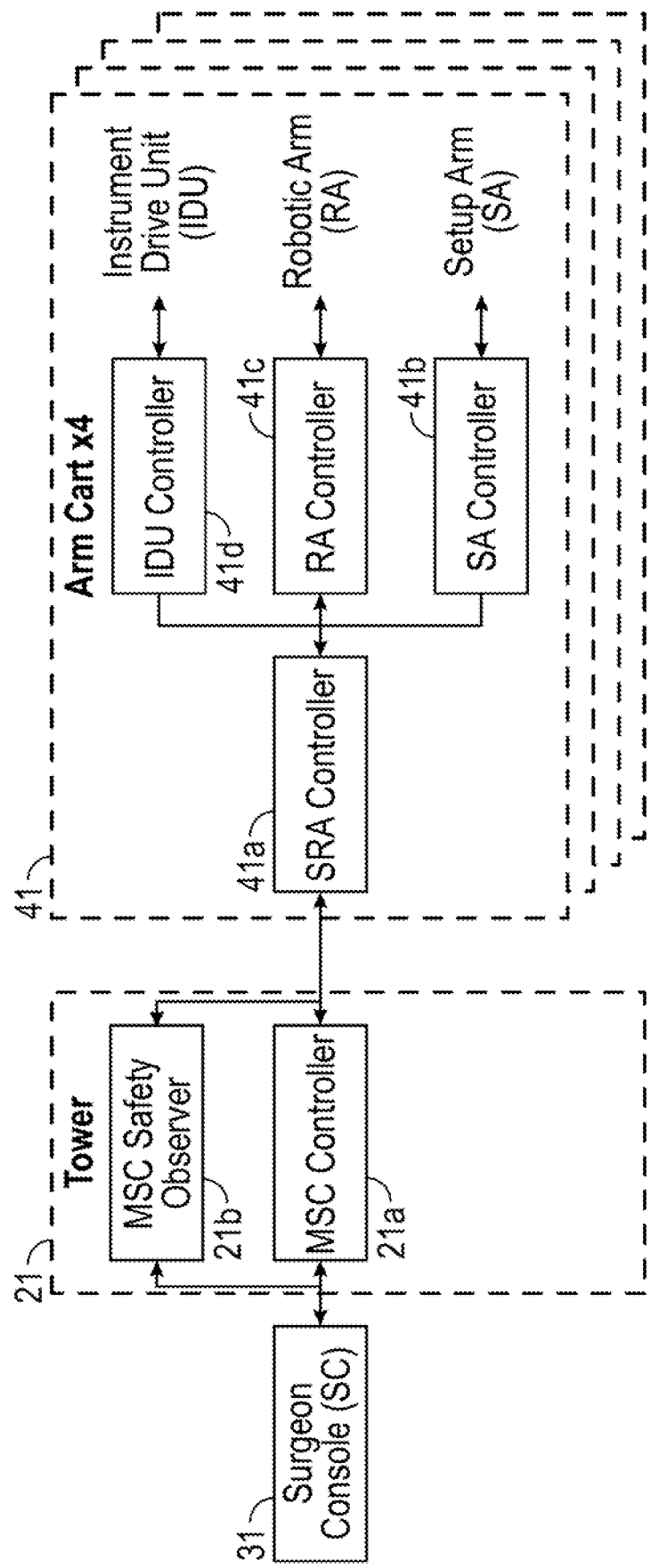
FIG. 4 is a schematic diagram of a computer architecture of the surgical robotic system of FIG. 1 according to the present disclosure.

With reference to FIG. 4, each of the computers 21, 31, 41 of the surgical robotic system 10 may include a plurality of controllers, which may be embodied in hardware and/or software. The computer 21 of the control tower 20 includes a controller 21a and safety observer 21b. The controller 21a receives data from the computer 31 of the surgical console 30 about the current position and/or orientation of the handle controllers 38a and 38b and the state of the foot pedals 36 and other buttons. The controller 21a processes these input positions to determine desired drive commands for each joint of the robotic arm 40 and/or the instrument drive unit 52 and communicates these to the computer 41 of the robotic arm 40. The controller 21a also receives back the actual joint angles and uses this information to determine force feedback commands that are transmitted back to the computer 31 of the surgical console 30 to provide haptic feedback through the handle controllers 38a and 38b. The safety observer 21b performs validity checks on the data going into and out of the controller 21a and notifies a system fault handler if errors in the data transmission are detected to place the computer 21 and/or the surgical robotic system 10 into a safe state.

The computer 41 includes a plurality of controllers, namely, a main cart controller 41a, a setup arm controller 41b, a robotic arm controller 41c, and an instrument drive unit (IDU) controller 41d. The main cart controller 41a receives and processes joint commands from the controller 21a of the computer 21 and communicates them to the setup arm controller 41b, the robotic arm controller 41c, and the IDU controller 41d. The main cart controller 41a also manages instrument exchanges and the overall state of the movable cart 60, the robotic arm 40, and the instrument drive unit 52. The main cart controller 41a also communicates actual joint angles back to the controller 21a.

The setup arm controller 41b controls each of joints 63a and 63b, and the rotatable base 64 of the setup arm 62 and calculates desired motor movement commands (e.g., motor torque) for the pitch axis and controls the brakes. The robotic arm controller 41c controls each joint 44a and 44b of the robotic arm 40 and calculates desired motor torques required for gravity compensation, friction compensation, and closed loop position control of the robotic arm 40. The robotic arm controller 41c calculates a movement command based on the calculated torque. The calculated motor commands are then communicated to one or more of the actuators 48a and 48b in the robotic arm 40. The actual joint positions are then transmitted by the actuators 48a and 48b back to the robotic arm controller 41c.

The IDU controller 41d receives desired joint angles for the surgical instrument 50, such as wrist and jaw angles, and computes desired currents for the motors in the instrument drive unit 52. The IDU controller 41d calculates actual angles based on the motor positions and transmits the actual angles back to the main cart controller 41a.

The robotic arm 40 is controlled as follows. Initially, a pose of the handle controller controlling the robotic arm 40, e.g., the handle controller 38a, is transformed into a desired pose of the robotic arm 40 through a hand eye transform function executed by the controller 21a. The hand eye function, as well as other functions described herein, is/are embodied in software executable by the controller 21a or any other suitable controller described herein. The pose of one of the handle controller 38a may be embodied as a coordinate position and role-pitch-yaw ("RPY") orientation relative to a coordinate reference frame, which is fixed to the surgical console 30. The desired pose of the instrument 50 is relative to a fixed frame on the robotic arm 40. The pose of the handle controller 38a is then scaled by a scaling function executed by the controller 21a. In embodiments, the coordinate position is scaled down and the orientation is scaled up by the scaling function. In addition, the controller 21a also executes a clutching function, which disengages the handle controller 38a from the robotic arm 40. In particular, the controller 21a stops transmitting movement commands from the handle controller 38a to the robotic arm 40 if certain movement limits or other thresholds are exceeded and in essence acts like a virtual clutch mechanism, e.g., limits mechanical input from effecting mechanical output.

The desired pose of the robotic arm 40 is based on the pose of the handle controller 38a and is then passed by an inverse kinematics function executed by the controller 21a. The inverse kinematics function calculates angles for the joints 44a, 44b, 44c of the robotic arm 40 that achieve the scaled and adjusted pose input by the handle controller 38a. The calculated angles are then passed to the robotic arm controller 41c, which includes a joint axis controller having a proportional-derivative (PD) controller, the friction estimator module, the gravity compensator module, and a two-sided saturation block, which is configured to limit the commanded torque of the motors of the joints 44a, 44b, 44c.

Figure 5:
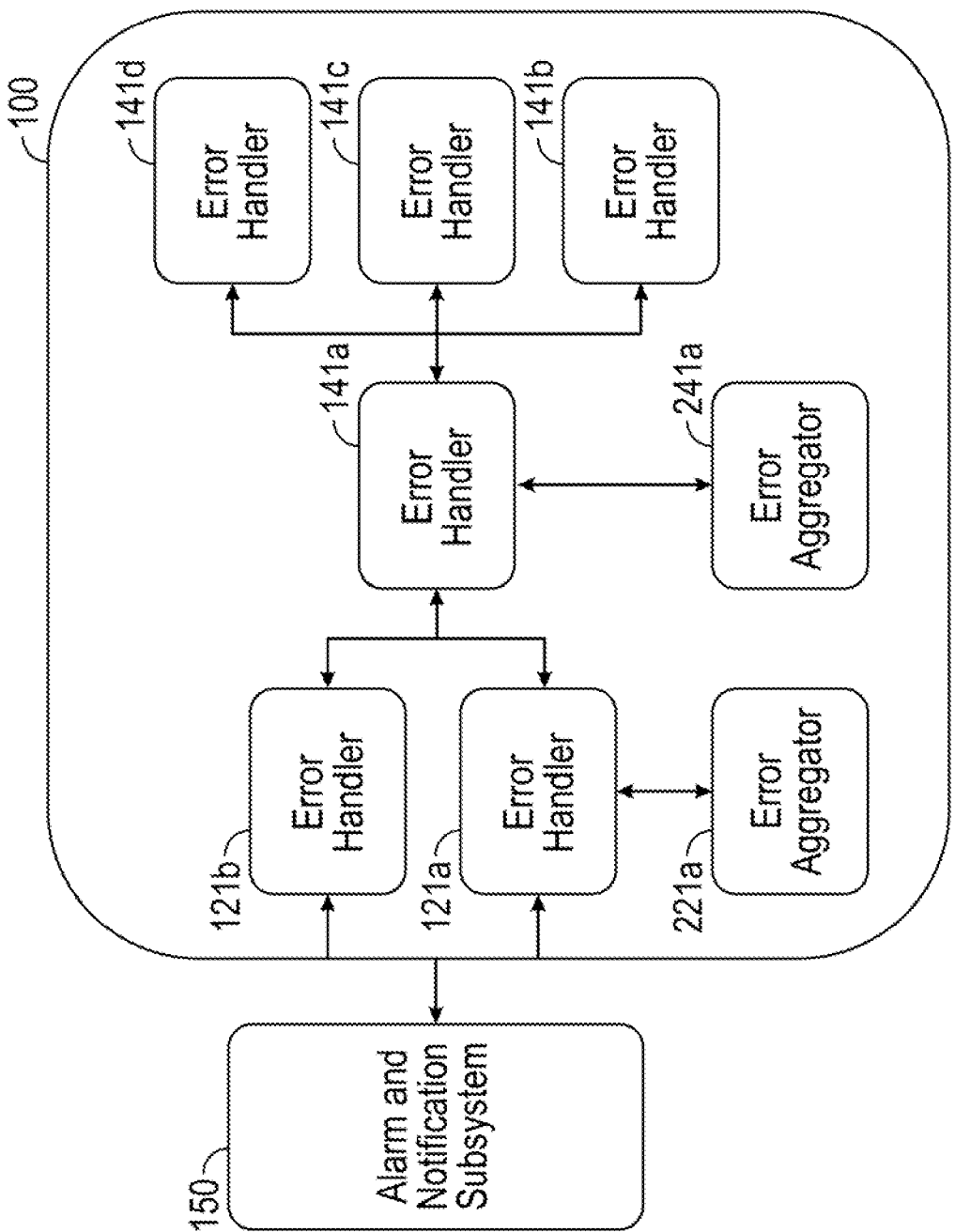
FIG. 5 is a schematic diagram of an error handler subsystem according to the present disclosure.

With reference to FIG. 5, the present disclosure provides an error handler network 100 which includes error handlers 121a, 121b, 141a, 141b, 141c, 141d, which may be embodied as software executable by each of the corresponding controllers: the controller 21a, the safety observer 21b, the main cart controller 41a, the setup arm controller 41b, the robotic arm controller 41c, and the IDU controller 41d, respectively. The error handler network 100 is a virtual network for transmitting signals communicating between multiple subsystems (e.g., controllers) to transmit information about errors and desired system reactions. Thus, if an error occurs at one component, then a controller, e.g., the main cart controller 41a, associated with that component reacts to the error with a preprogrammed response (e.g., preprogrammed action that places the component in a safe state). The controller, e.g., main cart controller 41a, also reports the error to other subsystems such as the safety observer 21b, the main cart controller 41a, and the setup arm controller 41b, and an alarm and notification subsystem. These subsystems then respond by initiating related safe behaviors. Safety behavior may also define an error response that includes a hard stop, e.g., complete shutdown of the robotic system 10, in which all modes (including manual control mode) are disabled for the remainder of the procedure until deactivation of the robotic system 10.

The error handlers 121a-b and 141a-d are networked together to coordinate a response across the system 10 and subsystem level in upstream/downstream and parent/child manner. Child subsystems (or child processes) refer to downstream, lower level subsystems such as the robotic arm controller 41c, the setup arm controller 41b, and IDU controller 41d. Mid-level subsystems refer to the main cart controller 41a of each of the mobile carts 60. The top-level subsystem is the controller 21a. Thus, all other error handlers 141a-141d are downstream from the error handler 121a and error handler 141a is the parent of the error handlers 141b-141d. The computer 31 of the surgical console 30 may also include a controller having an error handler, which is downstream of the error handler 121a and operates in the similar manner as the error handlers 141a-141d.

Figure 6:
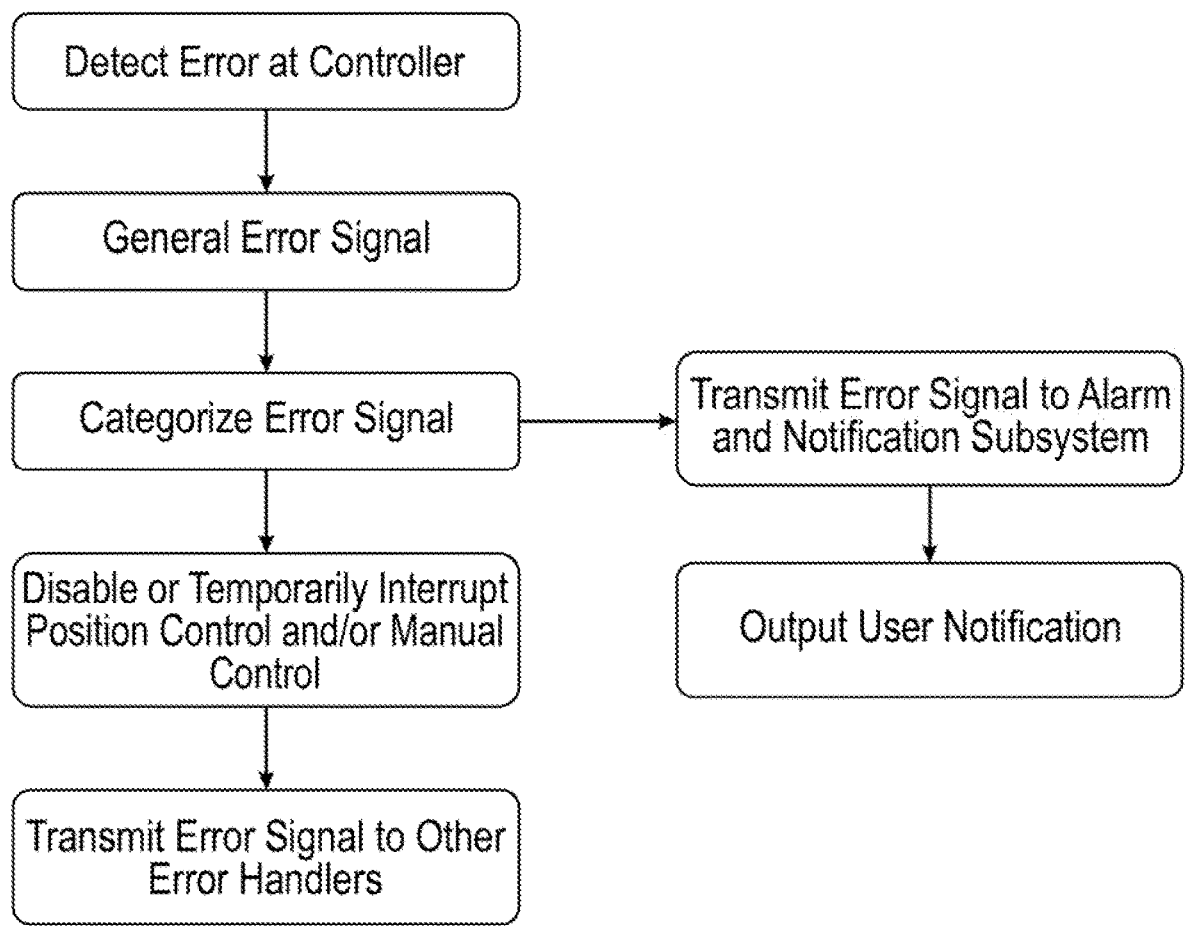
FIG. 6 is a flow chart of a method according to the present disclosure for handling error signals.

With reference to FIG. 6, initially, the error signals reported by the error handlers 121a-b and 141a-141d are categorized as an operable error or an inoperable error. As used herein, an operable error is an error during which normal function of the controllers (e.g., position control of the robotic arm controller 41c) is not affected and the user is simply notified that an error was detected. Inoperable error is an error in response to which position control of the robotic arm 40 and the surgical instrument 50 is disabled and manual control is also interrupted. Each of the controllers 21a and 41a-d reacts to the error signal based on the type of error signal. The reaction may have a predetermined duration for displaying a notification and/or a predetermined duration of how long an operational mode is disabled.

Responses to inoperable errors cause manual control of the robotic arms 40 and/or the surgical instruments 50 to be interrupted without permanently disabling the robotic arms 40 and the surgical instruments 50. Thus, if the user is actively using manual control when an inoperable error occurs then that instance of manual control is ended, and the user can let go of the button 53 and then reactivate the button 53 to re-enter manual control.

The error signals reported by the error handlers 121a-b and 141a-141d may further be classified as recoverable or nonrecoverable. Recoverability for a given error is defined at both the system level and the subsystem level. In embodiments, the error is defined as affecting the entire system 10 and one of the components, e.g., the movable cart 60. A system nonrecoverable error denotes that the entire system 10 cannot be recovered back to a usable state. A subsystem nonrecoverable error denotes that only one or more of the components where the error occurred cannot be recovered back to a usable state.

When a nonrecoverable error is encountered, manual control is temporarily interrupted and position control is disabled until the robotic system 10 is restarted. When a recoverable error is encountered, manual control is interrupted and position control is disabled only for a period of time, which is based whether the error is transient or persistent, and whether the error is dismissible.

Inoperable recoverable errors further include two categories: transient-type errors and persistent-type errors. Transient-type recoverable errors are further segregated into transient and dismissible errors. Persistent-type errors include nonrecoverable, persistent recoverable, and persistent-to-dismissible recoverable errors. Thus, the errors may be classified into the following types:

Nonrecoverable inoperable error—the affected subsystem notifies the user, disables position control, and interrupts manual control. Position control is disabled until the system is restarted.

Transient recoverable inoperable error—the affected subsystem notifies the user, interrupts position control, and interrupts manual control. All modes are available immediately after the error has occurred.

Persistent recoverable inoperable error—the affected subsystem notifies the user, disables position control, and interrupts manual control. Position control is disabled until the reason for the error is resolved (e.g., by user intervention).

Transient dismissible recoverable inoperable error—the affected subsystem notifies the user, disables position control, and interrupts manual control. Position control is disabled until the user acknowledges the notification, regardless of whether the reason for the error disappears.

Persistent dismissible recoverable inoperable error—the affected subsystem notifies the user, disables position control, and interrupts manual control. Position control is disabled until the reason for the error disappears and the user acknowledges the notification.

With reference to FIG. 5, each controller 21a and 41a-d uses a corresponding error handler 121a-b and 141a-d to communicate with other error handlers of the other controllers as well as with the state machines in its own controller. When an error occurs in a subsystem, that subsystem reacts by disabling/interrupting control modes and then sending messages to a neighboring subsystem via its corresponding error handler. The robotic arm controller 41c, the setup arm controller 41b, and IDU controller 41d communicate error signals to the main cart controller 41a, which then replies with confirmation of receipt and control commands. The main cart controller 41a also reports error information up to the controller 21a, which then replies with confirmation of receipt and nominal control commands as well. This communication combined with the designated recovery type affects the timing of when the controllers 41b-d can resume nominal functionality.

After detecting a problem, the error handler 141b, disables position control, and sends an alarm to an alarm and notification subsystem (ANS) 150, which may be embodied as a software application and is executed by the controller 21a. The ANS 150 is coupled to various inputs and outputs of the robotic system 10 and displays various audio and visual alarm and notifications on one or more of the displays 23, 32, 34, 69.

The error handler 141b then sends the error signal to the error handler 141a, which then sends a confirmation of receiving the error signal and initiates a hold protocol and stops position control. Error signals are also sent to the controller 21a, which recognizes the system-wide inoperable error and interrupts any robotic arms 40 in position control or manual control. The controller 21a also sends hold commands to all robotic arms 40 and sends a confirmation of receiving an error signal to the robotic arm 40. Additionally, the ANS 150 is also independently aware of the type of the error, e.g., that the error is a system persistent dismissible type. The controller 21a stops position control on any robotic arms 40 until the user dismisses the notification, and the user cannot dismiss the notification until the original problem is resolved.

Thus, all robotic arms 40 are locked out of position control as well as manual control. A notification appears on GUIs one or more of the displays 23, 32, 34, 69 with a graphical "dismiss" button to dismiss the error. A bedside assistant can reactivate the button 53 to get back into manual control. However, the user is not able to get back into position control because the error was a persistent dismissible type. After the problem responsible for the error independently disappears, the user can then dismiss the notification, and then the user is able to resume position control.

The error handler network 100 includes the following conditions, which are mapped to specific error states: manual mode for one robotic arm 40 is unavailable, position control for one robotic arm 40 is unavailable, position, manual, and hold modes for one robotic arm 40 are unavailable, and position control for all robotic arms 40 is unavailable. Conditions are mapped to the set of error states based on whether the error affects a subsystem, the robotic system 10, or both. Mapping also depends on error operability and recoverability. Some error states are set while the condition is true, while other error states are set as true when the condition occurs.

Inoperable recoverable errors are categorized into two categories: transient-type and persistent-type. Transient-type recoverability includes transient and dismissible errors. Persistent-type errors include nonrecoverable, persistent recoverable, and persistent to dismissible recoverable errors. In the transient-type inoperable errors, manual control and position control, as well as position control of all robotic arms 40, are interrupted but not disabled. In the persistent-type inoperable errors only manual control is interrupted and position control on all robotic arms 40 is disabled. The error state mapping for the system and subsystem persistent dismissible recoverable inoperable errors is the same as for persistent-type inoperable errors.

Regarding nonrecoverable errors, certain conditions are mapped to system and/or subsystem nonrecoverable errors. Nonrecoverable signals indicate when a nonrecoverable error has occurred on the subsystem. Each error signal generated by an error handler has its own signal pair, where the first error signal indicates subsystem (local) position control is nonrecoverable and the second error signal indicates system (global) position control is nonrecoverable. Nonrecoverable signals are set to being true during error state mapping and are transmitted upwards to parent subsystems. In the parent error handler (e.g., error handler 121*a* or 141*a*), nonrecoverable signals are analyzed by combining all of the nonrecoverable signals using an "or" operator (e.g., error handlers 141*b-d* as well as parent's nonrecoverable signals). If activated, these signals are latched until system deactivation.

The error handler network 100 also stores interrupt counters which when exceeded interrupt operation of the system 10 and/or any of the robotic arms 40. This allows the error handler network 100 to interrupt operation of the system 10 even when error states are dismissed. The error handlers 141*a-d* have a unique subsystem interrupt counter signal and a system interrupt counter. The counters represent how many errors have occurred in that subsystem. The counters are increased while the specific controller 41*a-d* is running continuously. The counters are reset once the specific controller 41*a-d* is shut down.

When an error occurs, that subsystem's error handler 141*b-d* increments the counter(s) and sends the signal upwards to the error handler 141*a* and/or the error handler 121*a*. The error handlers 121*a* and 141*a* detect when the counters are incremented and send interrupt signals to their state machines. The incremented counters are then sent to the child subsystems, e.g., the error handlers 141*b-d*. This confirmation transmission forms a cycle, which enables the child error handlers 141*b-d* to confirm that the messages were received by the upstream error handlers 121*a* and 141*a*.

The error confirmation cycle is used to end an active interruption of position control and/or manual control of the robotic arm 40. When any control mode is interrupted, error handlers 121*a* and 141*a* latch the error states as true until the downward counter matches the upwards counter. Error states may remain true for another reason (e.g., a persistent error), but the interrupt is ended.

The error handlers 121*a* may also verify the system interrupt counters. If a condition in a child error handler 141*b-d* maps to a system level inoperable error, the system interrupt counter is incremented and sent upwards to the controller 21*a*. The error handler 121*a* checks for increments, sends an interrupt signal to all controllers 41*a* of the mobile cart 60, and sends the increment counter back down to the error handler 141*a* of the problematic robotic arm 40. The child error handlers 141*b-d* may not receive a direct confirmation that the system-level message was received. Rather, since the child process is receiving commanded states from the controller 41*a*, the controller 41*a* keeps track of the counters and releases system-level error states appropriately. In embodiments, the error handlers 141*b-d* may also receive confirmation that the system-level messages were received.

The error handler 141*a* checks for subsystem interrupt counter increments, whereas the error handler 121*a* checks for system interrupt counter increments. The child error handler 141*b-d*, which detected an error continually marks error states as true for several ticks until the subsystem and system counters match. This system of counters forms a cycle which clears the pipeline of nominal commands. It also prevents a user from being able to command unavailable functionality in the window of time between an error being detected and the interrupt/error state signals reaching their destinations.

Error handlers 121*a-b* and 141*a-d* in all subsystems send messages to ANS 150 about what conditions rise and fall. Each condition has a unique alarm ID and ANS 150 is knows which movable cart 60 and/or the robotic arm 40 originates the alarm. The ANS 150 includes a database storing for each alarm ID a notification type and message and duration of the notification. The subsystem error handlers 141*a-d* include a database storing for each alarm ID corresponding controller reaction types and durations for the reaction.

With respect to dismissible errors, since the error handlers 121*a-b* and 141*a-d* are not aware of notification dismissals, the ANS 150 outputs a position control blocking signal which is sent to the controller 21*a*. The position control blocking signal is false by default. When a dismissible error occurs, ANS 150 sets the blocking signal to true and the error handler 121*a* uses this signal to make position control unavailable for all robotic arms 40. Even if the dismissible error did not occur in the controller 21*a*, the blocking signal from the ANS 150 to the error handler 121*a* causes the controller 21*a* to command nominal hold signals to all lower level state machines.

Alarm IDs are set and cleared through ANS 150. Alarms are set upon occurrence of certain conditions. Alarms are cleared upon condition ending. If the alarm is related to recoverable dismissible errors, then those alarms are cleared immediately after being set, because the ANS 150 utilizes the clear signal to enable a "dismiss" button (not shown) on a notification user interface displayed on one or more of the displays 23, 32, 34, 69. Without clearing the alarm through ANS 150, the user will not be able to dismiss the notification, and the error will not be transient.

For persistent dismissible errors, the alarms clear upon condition ending. Thus, the ANS 150 does not enable the "dismiss" button on the notification user interface until the condition ends, at which point the user is allowed to dismiss the notification and the ANS 150 stops blocking teleoperation by the controller 21*a*. An error signal mapped to a transient dismissible error may still be present, but the controller 21*a* is able to command position control again as soon as the user acknowledges the notification.

Each of the controller 21*a* and the controller 41*a* have an error aggregator 221*a* and 241*a* respectively, which aggregate errors from non-controller software in their respective domains, and forward those errors to the corresponding controller 21*a* or 41*a*. Error aggregators 221*a* and 241*a* may be embodied as software applications executable by each of the corresponding controllers 21a and 41a, respectively. The error aggregator 221a aggregates errors from all nodes of the control tower 20 and the surgical console 30 and forwards those errors to the controller 21a. The error aggregator 241a aggregates errors from non-controller software on each movable cart 60 and forwards those errors to the main cart controller 41a. The error aggregators 221a and 241a forward the errors to the error handlers 141b-d in the form of an array, which includes a counter of all active errors of a specific system and subsystem including their recoverability type. Upon receiving this array, the error handlers 141b-d identify any new errors that have occurred in the form of an increase in any of the counters, and also for any active errors in the form of non-zero counter values. These two conditions are used by the error handlers 141a-d to create the appropriate controller responses. The error handler response is the same as the response as if the error occurred in the respective controller that received the error report.

It will be understood that various modifications may be made to the embodiments disclosed herein. In embodiments, the sensors may be disposed on any suitable portion of the robotic arm. Therefore, the above description should not be construed as limiting, but merely as exemplifications of various embodiments. Those skilled in the art will envision other modifications within the scope and spirit of the claims appended thereto.

What is claimed is:

1. A surgical robotic system comprising:
   a control tower including a first controller having a first error handler, the first controller configured to detect a first error associated with the control tower and the first error handler configured to generate a first error signal based on the first error;
   a surgical console coupled to the control tower, the surgical console including a user input device configured to generate a first user input;
   a mobile cart coupled to the control tower, the mobile cart including a second controller and a second error handler, the second controller configured to detect a second error associated with the mobile cart and the second error handler configured to generate a second error signal based on the second error;
   a surgical robotic arm disposed on the mobile cart, the surgical robotic arm being operable in a position control mode in response to the first user input at the surgical console and a manual mode in response to a second user input, the surgical robotic arm including:
      a surgical instrument configured to treat tissue and being actuatable in response to the first user input; and
      a third controller having a third error handler, the third controller configured to detect a third error associated with the surgical robotic arm and the third error handler configured to generate a third error signal based on the third error; and
   an error handler network interconnecting the first error handler, the second error handler, and the third error handler, wherein the error handler network is configured to assign a category to one of the first error signal, the second error signal, or the third error signal and to temporarily interrupt the manual mode and disable the position control mode based on the assigned category.

2. The surgical robotic system according to claim 1, wherein
   the error handler network is configured to transmit the first error signal, the second error signal, and the third error signal between the first error handler, the second error handler, and the third error handler.

3. The surgical robotic system according to claim 1, wherein at least one of the control tower, the surgical console, or the mobile cart includes a display.

4. The surgical robotic system according to claim 3, further including an alarm and notification subsystem coupled to the error handler network, the alarm and notification subsystem configured to display a notification on the display.

5. The surgical robotic system according to claim 4, wherein the error handler network is configured reenable at least one the manual mode and the position control mode after the notification is dismissed by a user.

6. The surgical robotic system according to claim 1, wherein the error handler network is configured to store a counter that is incremented in response to at least one of temporary interruption of the manual mode or disabling of the position control mode.

7. The surgical robotic system according to claim 6, wherein each of the first error handler, the second error handler, and the third error handler stores an individual counter that is incremented in response to incrementing any of the individual counters.

8. The surgical robotic system according to claim 1, wherein the assigned category is a nonrecoverable, inoperable error.

9. A surgical robotic system comprising:
   a control tower including a first controller having a first error handler, the first controller configured to detect a first error associated with the control tower and the first error handler is configured to generate a first error signal based on the first error;
   a surgical console coupled to the control tower, the surgical console including a user input device configured to generate a first user input;
   a plurality of mobile carts coupled to the control tower, each of the mobile carts including a second controller and a second error handler, the second controller configured to detect a second error associated with the mobile cart and the second error handler is configured to generate a second error signal based on the second error;
   a plurality of surgical robotic arms, each of the surgical robotic arms being operable in a position control mode in response to the first user input at the surgical console and a manual mode in response to a second user input, wherein each of the surgical robotic arms is disposed on one mobile cart of the plurality of mobile carts, each of the surgical robotic arm including:
      a surgical instrument configured to treat tissue and being actuatable in response to the first user input; and
      a third controller having a third error handler, the third controller configured to detect a third error associated with the surgical robotic arm and the third error handler configured to generate a third error signal based on the third error; and
   an error handler network interconnecting the first error handler, the second error handler, and the third error handler, wherein the error handler network is configured to assign a category to one of the first error signal, the second error signal, or the third error signal and to temporarily interrupt the manual mode and disable the position control mode based on the assigned category.

10. The surgical robotic system according to claim 9, wherein the error handler network is configured to transmit the first error signal, the second error signal, and the third error signal between the first error handler, the second error handler, and the third error handler.

11. The surgical robotic system according to claim 9, wherein at least one of the control tower, the surgical console, or one of the mobile carts includes a display.

12. The surgical robotic system according to claim 11, further including an alarm and notification subsystem coupled to the error handler network, the alarm and notification subsystem configured to display a notification on the display.

13. The surgical robotic system according to claim 12, wherein the error handler network is configured reenable at least one the manual mode and the position control mode after the notification is dismissed by a user.

14. The surgical robotic system according to claim 9, wherein the error handler network is configured to store a counter that is incremented in response to at least one of temporary interruption of the manual mode and disabling of the position control mode and each of the first error handler, the second error handler, and the third error handler stores an individual counter that is incremented in response to incrementing any of the individual counters.

15. The surgical robotic system according to claim 9, wherein the surgical console includes:
 a fourth controller having a fourth error handler, the fourth controller configured to detect a fourth error associated with the surgical console and the fourth error handler is configured to generate a fourth error signal based on the fourth error.

16. The surgical robotic system according to claim 9, wherein the assigned category is a nonrecoverable, inoperable error.

\* \* \* \* \*